United States Patent [19]

Luk et al.

[11] 4,152,337

[45] May 1, 1979

[54] KETONES

[75] Inventors: Kong Luk, Cranleigh; John P. Clayton, Horsham; Norman H. Rogers, Rudgwick, all of England

[73] Assignee: Beecham Group Limited, Great Britain

[21] Appl. No.: 873,395

[22] Filed: Jan. 30, 1978

Related U.S. Application Data

[62] Division of Ser. No. 803,467, Jun. 6, 1977, Pat. No. 4,102,904.

[30] Foreign Application Priority Data

Jun. 15, 1976 [GB] United Kingdom ............... 24712/76
Sep. 29, 1976 [GB] United Kingdom ............... 40472/76
Mar. 1, 1977 [GB] United Kingdom ................ 8647/77

[51] Int. Cl.$^2$ .......................................... C07D 309/22
[52] U.S. Cl. ............................................. 260/345.9 R
[58] Field of Search ................................. 260/345.9 R

[56] References Cited

U.S. PATENT DOCUMENTS 4,071,536   1/1978   Barrow et al. ...................... 424/283

OTHER PUBLICATIONS

Sandler et al., Organic Functional Group Preparations, pp. 48–51 (1968).

*Primary Examiner*—Nicky Chan
*Attorney, Agent, or Firm*—Jacobs & Jacobs

[57] ABSTRACT

A novel acid of formula:

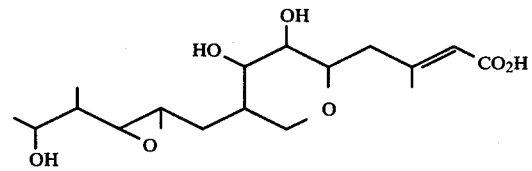

which is termed "monic acid" and is prepared from pseudomonic acid, is a useful intermediate for the preparation of esters thereof.

1 Claim, No Drawings

KETONES

CROSS-REFERENCE

This is a division of Ser. No. 803,467 filed June 6, 1977 now U.S. Pat. No. 4,102,904.

This invention relates to chemical intermediates and in particular to an allylic carboxylic acid and salts thereof which are useful for the preparation of a class of antibacterially active esters.

Pseudomonic acid has the structure (I):

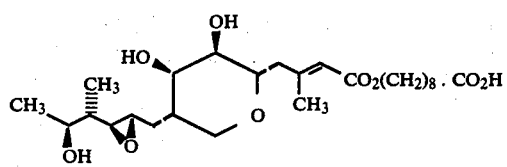

and is disclosed as having antibacterial activity in British Pat. No. 1,395,907. It has now been found that the allylic carboxylic acid moiety of the molecule is useful for preparing other esterified derivatives.

Accordingly, the present invention provides a compound of formula (II):

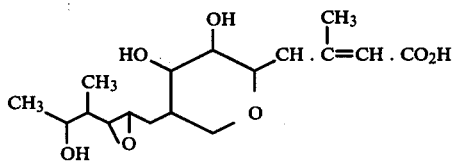

or a salt thereof.

The compound of formula (II) wherein the double bond is in the E configuration, we have designated "monic acid" and it will be referred to as such in this specification. The corresponding Z-isomer is termed "isomonic acid". It is believed that monic acid has the absolute sterochemistry as shown in formula (IIA):

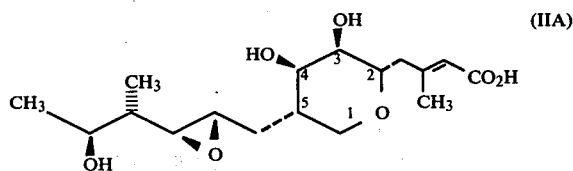

(The numbering is shown for the tetrahydropyran ring).

The salts of compound (II) may be pharmaceutically acceptable, but need not be, as the utility of compound (II) is as a chemical intermediate. Suitable salts of the compound include metal salt, e.g. aluminium, alkali metal salts, such as sodium or potassium, alkaline earth metal salts such as calcium or magnesium, and ammonium or substituted ammonium salts for example those with lower alkylamines such as triethylamine, hydroxy-lower alkylamine such as 2-hydroxyethylamine, bis-(2-hydroxyethyl)-amine, or tri-(2-hydroxyethyl)-amine, cycloalkylamines such as bicyclohexylamine, or with procaine, dibenzylamine, N,N-dibenzyl-ethylenediamine, 1-ephenamine, N-ethylpiperidine, N-benzyl-$\beta$-phenethylamine, dehydroabietylamine, N,N'-bis-dehydroabietylethylenediamine, or bases of the pyridine type such as pyridine, collidine, or quinoline.

The compound (II) of this invention incorporates a trisubstituted double bond and may therefore exist in both the E (the natural) and Z (or iso) geometrical forms. It is to be understood that both geometrical isomers of the compound of formula (II) are included within the scope of this invention, as well as mixtures of the two isomers. However, because in general the E-isomer of a particular esterified derivative of compound (II) has the greater activity, it is preferable to employ that isomer.

The compounds of the present invention may be prepared from the intermediate ketone of formula (III) by any method known to convert a ketone into an $\alpha,\beta$-unsaturated acid. One such process comprises reacting a compound of formula (III) in which the hydroxyl groups may be protected with a compound of formula (IV) or (V):

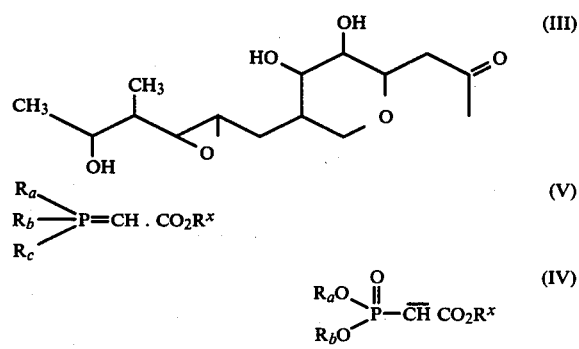

in which formulae (IV) and (V) the symbols $R_a$, $R_b$ and $R_c$ are the same or different and each is lower alkyl, aryl or aralkyl, and $R^x$ is hydrogen, or a carboxyl-protecting group which is removable under neutral conditions; and subsequently removing any hydroxyl or carboxyl-protecting groups.

The preferred embodiment of this process for preparing the compounds of the invention comprises reacting compound (III) with compound (IV). Preferably in this case $R_a$ and $R_b$ are methyl or ethyl. In the case when compound (III) is reacted with compound (V), then $R_a$, $R_b$ and $R_c$ are preferably all phenyl.

The reaction is usually carried out in an inert solvent such as dimethylformamide, hexane, benzene, tetrahydrofuran for example, at a temperature of from about 10° C. to about 100° C., preferably under an inert gas such as nitrogen. Under these conditions the reaction proceeds smoothly over a period of from a few minutes tp a few hours and the product may be isolated by any of the usual techniques e.g. solvent evaporation or anti-solvent precipitation followed by filtration. In many cases the reaction may be carried out in a solvent in which the product is insoluble and in such cases the precipitated solid may be collected by filtration. Purification of the product may be by any of the usual chromatographic or recrystallisation techniques.

In the case where compound (III) is reacted with compound (IV) and the group $R^x$ is hydrogen, it is convenient to treat the compound (IV) firstly with a strong base. For example sodium hydride may be used which produces the disodium salt;

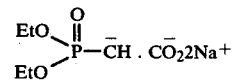

which is then reacted with the compound (III).

Alternatively, the group R$^x$ may be carboxyl protecting group which is removed after the reaction. Because of the sensitivity of the molecule to both acid and base, such a carboxyl-protecting group must be removable under suitably mild conditions. Suitable carboxyl-protecting groups include the 2,2,2-trichloroethyl ester, (which may be removed with zinc in a lower alcohol, especially methanol) phenyl, pentachlorophenyl, benzyl and t-butyl ester groups. Other suitable carboxyl-protecting groups are silyl groups. In this case the carboxylic acid is reacted with a silylating agent such as a halosilane or silazane of the formula:

L$_3$ Si U;    L$_2$ Si U$_2$;    L$_3$ Si N L$_2$;

L$_3$ Si NH Si L$_3$; L$_3$ Si NH CO L; L$_3$ Si NH CO NH Si L$_3$;

L NH CO NH Si L$_3$; L C OSi L$_3$
                        ‖
                       NSiL$_3$ wherein U is halogen and the various groups L which may be the same or different, each represents hydrogen, or alkyl, alkoxy, aryl or aralkyl. A preferred silylating agent is N,O-bis(trimethylsilyl)acetamide, which produces the trimethylsilyl derivative of the acid.

Prior to the above process of this invention, it may be desirable to protect the hydroxyl groups in compound (III). Although the reaction with the compound (IV) or (V) is possible without hydroxyl protection, in general higher yields of the product (II) are formed if the hydroxyl groups are protected. Again such protecting groups must be removable under suitably mild conditions and suitable groups include silyl groups produced from a silylating agent as discussed above. Particularly suitable hydroxyl-protecting groups include trimethylsilyl, t-butyldimethylsilyl, methylthiomethyl, A preferred hydroxyl-protecting group is trimethylsilyl, as it is readily removed on completion of the reaction.

The compounds (II) may also be prepared by reacting the ketone of formula (III) with:

(a) an ethynyl ether of formula (VI);

HC≡C—OR$^x$ (VI)

wherein R$^x$ is as defined above and subsequently treating the product with acid;

(b) an α-lithium carboxylic acid derivative of formula (VII):

wherein R$^x$ is as defined above and R$^y$ is a silyl group, preferably trimethylsilyl;

(c) a malonic acid derivative of formula (VIII):

wherein R$^x$ is as defined above in the presence of titanium chloride and pyridine;

(d) a reagent to convert compound (V) to an enamine and subsequently reacting the enamine with a malonic acid derivative of formula (IX):

wherein R$^x$ is as defined above.

The compound of formula (III) is a valuable intermediate and also forms part of this invention.

The compound may be produced by a process which comprises treating pseudomonic acid of formula (I) above, or an ester thereof, with ozone.

This reaction may be performed without protecting the hydroxyl groups in pseudomonic acid and is preferably carried out at a low temperature such as −50° C. to −80°, suitably −70° C. to −80° C.

It will be noted that the triacetate derivative of compound (III) was disclosed in British Patent No. 1,395,907 during the structure elucidation of pseudomonic acid. However, the compound (III) is not disclosed therein and there is no suggestion of a method of removing the acetate groups in order to prepare compound (III).

The compound of formula (II) may also be prepared by chemical or enzymic hydrolysis of an ester of a compound of formula (II) under conditions which do not disrupt the rest of the molecule.

Esters of the compound of formula (II) are disclosed in our corresponding application of even date and any such ester may be employed for hydrolysis to compound (II). Normally it is preferable to employ the naturally-occurring ester, that is pseudomonic acid of compound (I).

A particularly advantageous method of carrying out this hydrolysis process for the preparation of compound (II) comprises:

(a) protecting a compound of formula (X):

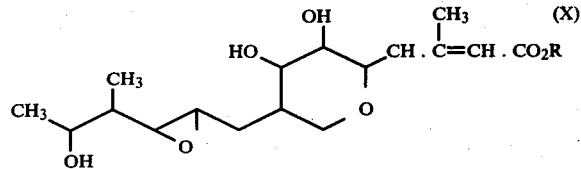

wherein R represents an ester-forming radical, with a hydroxyl-protecting group which is stable to alkaline conditions and is removable under mild acid conditions;

(b) hydrolysing the ester radical —CO$_2$R from resulting compound under alkaline conditions; and (c) removing the hydroxyl-protecting group.

The choice of hydroxyl-protecting group is important in the present process because the molecule of formula (II) [and (X)] is susceptable to rearrangement under the alkaline conditions necessary to carry out the ester hydrolysis step. It may only be necessary to protect the hydroxyl group at position 4 on the molecule, but this is most conveniently effected either by protecting the glycol moiety, that is the hydroxyl groups at positions 3 and 4, by a single protecting group, or by protecting all three hydroxyl groups in the molecule.

The choice of a suitable hydroxyl-protecting group is also important and must (a) react readily with the hydroxy group; (b) be stable under alkaline conditions and (c) be either removable under mild acidic conditions which again do not cause rearrangement of the molecule or converted under mild acid conditions to a different group which is removable under alkaline or enzymic conditions.

Preferably the glycol moiety is protected and suitable reagents for forming the hydroxy-protecting group include compounds of formula (XI):

wherein $R^3$ is hydrogen or a $C_{1-6}$alkyl group and $R^4$, $R^5$ and $R^6$ independently represent a $C_{1-6}$ alkyl group.

The use of the compound of formula (XI) in the hydrolysis process is illustrated in Scheme A, where X represents the residue:

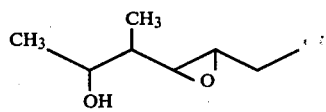

(wherein the hydroxyl group may also be protected during the reaction).

(XIVA) and (XIVB) are formyl groups and are readily removed under mild alkaline conditions to re-generate the free hydroxyl group, without disrupting the rest of the molecule. If the group $R^3$ is a $C_{1-6}$ alkyl group the corresponding $C_{1-6}$ alkanoyl protecting groups in compounds (XIVA) and (XIVB) may also be removed by either a chemical or enzymatic hydrolysis procedure.

The groups $R^4$, $R^5$, and $R^6$ may be for example, methyl, ethyl, n- or iso-propyl, n- or iso-, sec- or tert--butyl. Preferably $R^4$, $R^5$, and $R^6$ are all the same and each represents a methyl group. The group R is conveniently —$(CH_2)_8CO_2H$, that is the starting material of formula (X) is pseudomonic acid.

It is pointed out that the formation of compound (XII) in Scheme A introduces an additional optically active centre into the molecule and the compound (XII) is normally produced as a mixture of two epimers. It is unnecessary to separate these epimers and the optically active centre is removed when this glycol protecting group is eventually removed.

The alkaline hydrolysis of step (b) above may be carried out by any conventional method. Suitable bases for this step include inorganic bases, especially alkali metal hydroxides, such as sodium hydroxide, potassium

SCHEME A

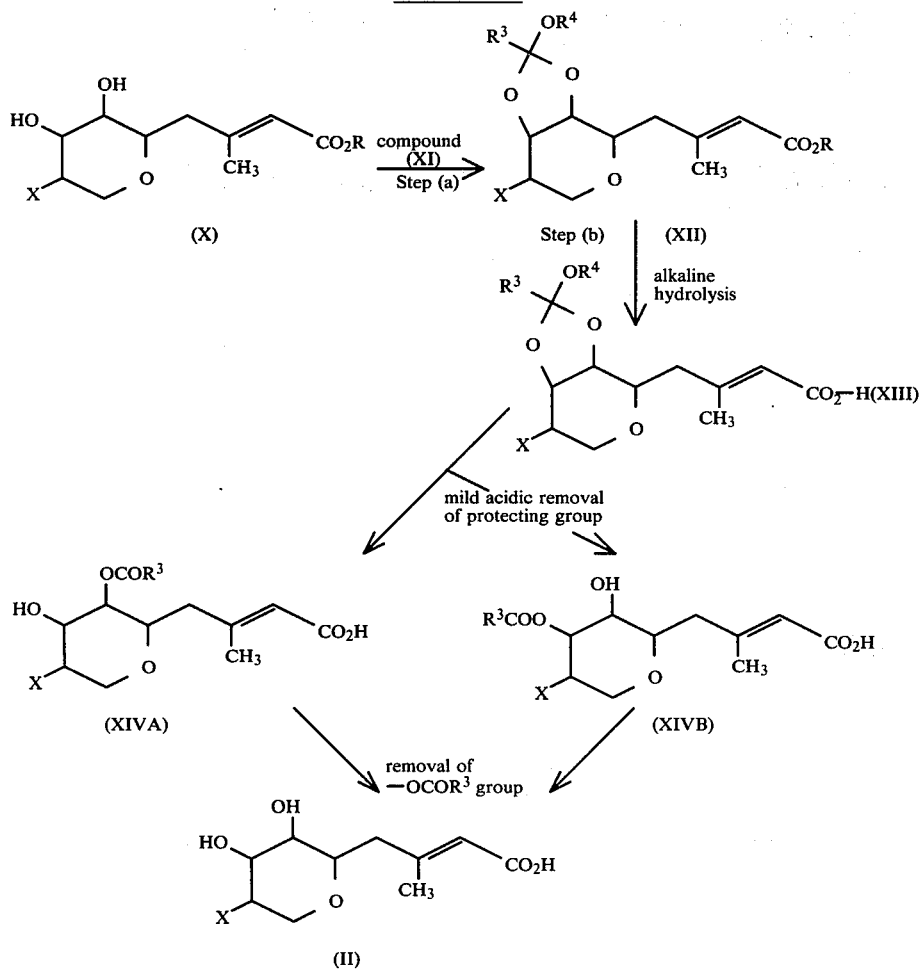

The group $R^3$ may be for example hydrogen, methyl ethyl, n- or iso-propyl. Most suitably, $R^3$ represents hydrogen so that the compound of formula (XI) is a trialkyl orthoformate. In such a case, the groups remaining attached to the hydroxyl groups in formulae hydroxide, carbonates such as potassium carbonate and bicarbonates such as sodium bicarbonate or potassium bicarbonate. The reaction is generally carried out at ambient temperature for a period of from 1 to 10 hours. A suitable temperature is from 20° to 80° C. preferably from 50° to 80°, especially from 60° to 70° C.

The hydroxyl-protecting group is then removed by a conventional method for the particular hydroxyl-protecting group, and the compound of formula (II) is isolated.

The hydroxyl-protecting group may be such that it can be removed directly or alternatively, it may be converted by mild acid treatment into a different protecting group which is then removable under alkaline conditions. This latter approach is illustrated in Scheme A wherein the glycol protecting group is converted by acid to the group —OCOR$^3$ which is then removed.

The hydroxyl-protecting group is then removed by a conventional method for the particular hydroxyl-protecting group, and the compound of formula (II) is isolated.

The compound (II) is a valuable intermediate for the preparation of antibacterially active esters thereof as described in our co-pending application Ser. No. 803,466, filed June 6, 1977.

The following Examples illustrate the present invention:

EXAMPLE 1

Preparation of 2S-Acetonyl-3R,4R-dihydroxy-5S-(2S,3S-epoxy-5S-hydroxy-4S-methylhexyl)-2,3,5,6-tetrahydropyran (compound A)

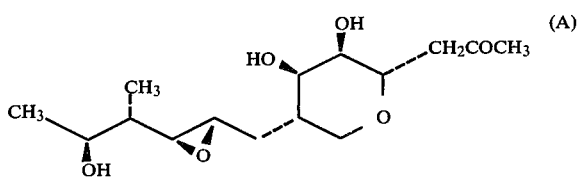

Ozonised oxygen (ca 1%) was bubbled through a solution of methyl pseudomonate (0.514 g) in methanol (8 ml) and pyridine (2 drops) at −78° C. for 0.5 hour (when blue colour developed). The excess ozone was blown off by dry nitrogen at −78° C. Triethyl phosphite (80%. 0.3 ml) was then added and the reaction mixture was allowed to come to room temperature. The solvent was removed at room temperature in vacuo and the residue was chromatographed over silica gel (20 g). Elution of the column with chloroform-methanol (93:7) at the rate of 2 ml min$^{-1}$ gave the title compound (0.299 g), m.p. 85°–86° (from chloroform), $[\alpha]_D^{20}$+11.9° (c, 1.0,CHCl$_3$), $\nu$max. (CHCl$_3$) 1708, 1112, 1080, and 1050 cm$^{-1}$.

EXAMPLE 2

Preparation of 4-[3R,4R-dihydroxy-5S-(2S,3S-epoxy-5S-hydroxy-4S-methylhexyl)-2,3,5,6-tetrahydropyran-2S-yl]-3-methyl-but-2E-enoic acid (monic acid)

(a) From Pseudomonic Acid (without protection)

Sodium pseudomonate (10 mg) and potassium carbonate (15 mg) was dissolved in water (2 ml). The resulting solution was heated to 60° C. and the reaction monitored by analytical high pressure liquid chromatography which after 1½ hours showed that optimum conversion to monic acid had occurred.

To confirm the presence of monic acid, the reaction mixture was cooled, diluted with water (3 ml) saturated with sodium chloride, layered with ethyl acetate (10 ml) and the pH adjusted to 2.0 with rapid stirring. The organic layer was separated and the aqueous phase re-extracted with ethyl acetate (2×10 ml). The colourless ethyl acetate extracts were combined, treated with excess ethereal diazomethane and evaporated to dryness. The resulting mixture of esters were examined by h.p.l.c. in several solvent systems. The major peaks in the chromatogram were shown to have identical retention times with authentic samples of methyl monate and methyl pseudomonate, thereby confirming the presence of monic acid together with starting pseudomonic acid in the hydrolysate.

(b) From Methyl Monate

A solution of methyl monate (10 mg) in methanol (0.5 ml) was added to a solution of potassium carbonate (15 mg) in water (0.5 ml). The combined solution was heated to 60° C. After ½ hour, comparison of peak retention times with authentic monic acid by h.p.l.c. analysis confirmed the presence of monic acid in hydrolysate.

EXAMPLE 3

Preparation of monic acid from ketone (A) by Wittig condensation (i) Diethyl carboxymethylenephosphonate Triethyl phosphonoacetate (44.8 g, 0.2 M) was dissolved in 1N sodium hydroxide solution (200 ml; 0.2 M) and stirred at room temperature overnight. The pH was adjusted from 9.0 to 1.0 with dilute hydrochloric acid. The solution was saturated with sodium chloride and extracted with ethyl acetate (3×100 ml). The latter was washed with saturated brine, dried over magnesium sulphate, filtered and evaporated to dryness in vacuo to give a viscous, colourless oil, which crystallized to a white solid when kept below room temperature (37.4 g; 96%). Thin layer chromatography revealed one component in chloroform at Rf=0.02 as visualised with iodine vapour. $n_D^{23}$=1.3900.$\delta$ (CDCl$_3$) 9.33 (1H, s, CO$_2$H), 4.07 (4H, octet, Me—CH$_2$—O—P, $J_{HH}$=6 Hz, $J_{HP}$=8 Hz), 2.88 (2H, d, P—CH$_2$—CO$_2$H,$J_{HP}$=22 Hz) and 9.25 (6H, t, CH$_3$—CH$_2$, J=6 Hz). Irradiation at $\delta$ 9.25 produces a doublet at 4.07 with $J_{HP}$=8 Hz, $\nu$max(-film) 1730 (C=O Str.), 1230 (P=O str.), 1170 (P—O vib.), 1050 (P—O vib.) cm$^{-1}$. (Found: C, 37.10; H, 7.07; P, 15.66%; C$_6$H$_{13}$PO$_5$ requires C, 36.74; H, 6.69; P, 15.79%).

(ii) Monic acid

N,O-Bistrimethylsilylacetamide (1.52 ml; 6 mM) was added to a solution of 2-acetonyl-3,4-dihydroxy-5-(5-hydroxy-2,3-epoxy-4-methylhexyl)-2,3,5,6-tetrahydropyran (302 mg; 1 mM) in dry acetonitrile (6 ml). The solution was stirred at room temperature for 1 hour followed by evaporation to dryness in vacuo at 40° C. The oily residue was dissolved in dry dimethylformamide (6 ml) for use in the next stage. Sodium hydride (114 mg; 80% pure; 3.8 mM) was added portionwise over ½ hour to a solution of diethyl carboxymethylene phosphonate (392 mg; 2 mM) in dry dimethylformamide (5 ml) at 0° under dry nitrogen. The mixture was stirred at for a further 2 hours. The solution of the silylated ketone above was added dropwise to this mixture at 0° C. under nitrogen and the resulting reaction mixture stirred overnight at room temperature. The latter was evaporated to dryness and the dark residue dissolved in water (10 ml) and ethanol (10 ml) and the pH adjusted to 1.8. After 5 min., at room temperature the solution was diluted with water (15 ml) saturated with sodium chloride and extracted with ethyl acetate (4×10 ml). The latter was washed with brine, dried over magnesium sulphate, filtered and evaporated to dryness in vacuo to give monic acid. A sample of the resulting oil mixture was dissolved in ethyl acetate and treated with diazomethane, thus converting the monic acid present into methyl monate. The presence of the latter was confirmed by 4 analytical h.p.l.c. comparisons with authentic pure methyl monate.

EXAMPLE 4

4-[3R,4R-Dihydroxy-5S-(2S,3S-epoxy-5S-hydroxy-4S-methylhexyl)-2,3,5,6-tetrahydropyran-2S-yl]-3-methyl-but-2E-enoic acid (Monic Acid) (with protection)

Pseudomonic acid (10 g; 20 mM) was dissolved in trimethylorthoformate (50 ml). p-Toluenesulphonic acid (20 mg) was added and the solution was stirred at room temperature for ½ hour, followed by evaporation to dryness in vacuo. The resulting oil was dissolved in 1N sodium hydroxide solution (100 ml; 100 mM) and the solution stirred at 65° C. for 2 hours. After completion of the hydrolysis (hplc) the solution was cooled and the pH adjusted to 7.0 with hydrochloric acid. Methanol (75 ml) was added, the pH was adjusted to 2.0 with 5N hydrochloric acid and the reaction mixture stirred at room temperature for 0.25 hour. The pH was re-adjusted to 9–9.5 with sodium hydroxide solution and maintained until complete hydrolysis of the O-formate (c.a. 3 hours at room temperature; hplc). The pH was adjusted to 7.0 and the solution evaporated to small bulk (10–20 ml), saturated with sodium chloride, layered with ethyl acetate and with stirring the pH was adjusted to 3.0. The ethyl acetate layer was separated, washed with saturated brine, dried over magnesium sulphate and evaporated to an oil, which was dissolved in water by addition of 1N sodium hydroxide solution to pH 7.5. The resulting solution of sodium monate and sodium 9-hydroxynonanoate was evaporated to dryness in vacuo (12.64 g). This solid was extracted with ethanol (2×50 ml) and filtered. The ethanol filtrate was evaporated to dryness to give sodium monate (9.62 g) as a white solid. The latter was dissolved in water with ethyl acetate and acidified to pH 3.0. The ethyl acetate extract was washed with saturated brine, dried over magnesium sulphate and evaporated in vacuo to an oil (8.48 g). Trituration with dry ether afforded monic acid as a white solid, which was collected and dried (2.62 g; 38%), m.p. 133°–135° C. (crystals from ethanol m.p. 146°–147° C.) (Found: C, 59.0; 8.2% $C_{17}H_{28}O_7$ requires C, 59.3; H, 8.2%). Tlc revealed a single component Rf=0.44 in chloroform, acetone, acetic acid 12:5:3 and a single peak by hplc $[\alpha]_D$ −13°(c, 1.0EtOH) and −20° (c, 1.0 1% NaHCO₃), νmax (KBr) 3300, 2960, 2950, 1690, 1640, 1450, 1250cm⁻¹, λmax 221 nm (εm 11,200), $\delta_H$ (d6-DMSO) 5.55 (1H,s,=C<u>H</u>),

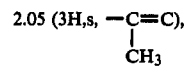

1.05 (3H,d,>CHC<u>H</u>₃) and 0.80 (3H,d,>CHC<u>H</u>₃) $\delta_C$ (d⁶-DMSO) (2 signals under the DMSO peaks) 167.3, 156.4, 117.6, 74.5, 69.4, 68.2, 66.7, 64.6, 59.0, 54.6, 37.3, 31.47, 20.0, 18.4 and 11.6, m/e 227 (82%, M+—H-2O—C₅H₇O₂), 141 (43%) 111 (100%).

EXAMPLE 5

Sodium Monate

Monic Acid prepared in Example 4 (3.44 g; 1 mM) was dissolved in water (10 ml). N/10 sodium hydroxide solution (10 ml; 1 mM) was added to the stirred solution until complete solution was obtained (pH 7.5). The latter was freeze dried and finally dried in vacuo over P₂O₅. (3.66 g; 100%). $[\alpha]_D$−20° (c,1.0 H₂O) νmax (KBr) 3400, 2970, 1650, 1550cm⁻¹., λmax (EtOH) 214 nm (εm 14,600), $\delta_H$(d⁶-DMSO) 5.16 (1H,s,=C<u>H</u>), 1.95 (3H,s,=CC<u>H</u>₃), 1.05 (3H,d,>CHC<u>H</u>₃) and 0.79 (3H,d,>CHC<u>H</u>₃).

Improved Isolation of Monic Acid.

Pure Crystalline pseudomonic acid (1.00 gm; 2 mM) was dissolved in trimethylorthoformate (10 ml) and stirred at R.T. for 30 minutes with p-toluene sulphonic acid (10 mg). The solvent was then removed at reduced pressure and the residual oil immediately dissolved in 1N NaOH (10 ml; 10 mM). The solution was stirred at 65° C. for 3 hours, then cooled and the pH adjusted to 7.0 with conc. HCl. Methanol (10 ml) was added, the pH was adjusted to 2.0 with 5N HCl and the solution was stirred at R.T. for 15 minutes. The pH was then raised to an maintained at 9.0–9.5 with NaOH for 3 hours, when HPLC indicated complete hydrolysis of the O-formate. The pH was adjusted to 7.0 and the solution evaporated to dryness at reduced pressure. The residual solid was dissolved in water (20 ml), saturated with NaCl, layered with ethyl acetate and acidified to pH 3. The organic layer was separated and the aqueous layer further extracted with 5×50 ml ethyl acetate. The combined organic extracts were dried over anhydrous MgSO₄ and the solvent removed at reduced pressure to yield a yellow oil (1.377 gm; 1433/50/1.) Trituration with dry diethyl ether gave the monic acid (>90% pure by HPLC and TLC) as a white solid (0.393 gm; 1433/50/2). A further 0.146 gm (1433/50/3) white solid was obtained from the mother liquors. Total yield =0.539 gm (78%) M. pt. 130°–133° C. The product was identical to authentic monic acid by HPLC and TLC (chloroform/acetate/acetic acid 50:50:7).

What we claim is:
1. A compound of formula (III):

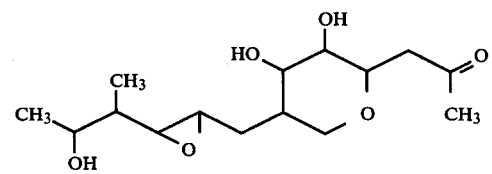

* * * * *